(12) United States Patent
Sprecker et al.

(10) Patent No.: US 6,362,141 B1
(45) Date of Patent: Mar. 26, 2002

(54) INDANYL DERIVATIVES

(75) Inventors: Mark A. Sprecker, Sea Bright; Richard A. Weiss, Livingston; Robert P. Belko, Monroe; Ellen Ann Molner, Kinnelon, all of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/948,511

(22) Filed: Sep. 6, 2001

Related U.S. Application Data

(62) Division of application No. 09/770,739, filed on Jan. 26, 2001.

(51) Int. Cl.⁷ .............................. C11D 3/20; A61K 7/46
(52) U.S. Cl. ..................... 510/105; 510/104; 512/14; 512/18
(58) Field of Search .................. 510/104, 105; 512/14, 18

(56) References Cited

U.S. PATENT DOCUMENTS

| | | | |
|---|---|---|---|
| 4,534,891 A | 8/1985 | Boden et al. | |
| 5,403,823 A | * 4/1995 | Frank | ............ 512/17 |
| 5,530,150 A | 6/1996 | Takaya et al. | |
| 5,552,379 A | * 9/1996 | Winter et al. | ............ 512/12 |

FOREIGN PATENT DOCUMENTS

| | | | |
|---|---|---|---|
| DE | 2 053 736 | | 5/1972 |
| DE | 2 132 414 | | 1/1973 |
| GB | 2233645 A | * | 1/1991 |
| JP | 11-80111 | * | 3/1999 |

OTHER PUBLICATIONS

Corma, et al, "Formylation and Hydrolysis of Acetals Catalysed by Acid Faujasites", Applied Catalysis, 59 (1990), 333–340.

Doyle, et al, Hydroformylation of Tricarbony ($\eta^6$–Styrene)Chromium and Related Compounds, Tetrahedron Letters, vol. 30, pp. 5357–5360.

* cited by examiner

Primary Examiner—John Hardee
(74) Attorney, Agent, or Firm—Joseph F. Leightner

(57) ABSTRACT

The present invention is directed to indanyl derivatives and the use of the indanyl derivatives in creating fragrances, and scents in items such as perfumes, colognes and personal care products.

6 Claims, No Drawings

INDANYL DERIVATIVES

Div of Ser. No. 09/770,739, Jan. 26, 2001, now allowed.

FIELD OF THE INVENTION

The present invention relates to new chemical entities and the incorporation and use of the new chemical entities as fragrance chemicals.

BACKGROUND OF THE INVENTION

There is an ongoing need in the fragrance industry to provide new chemicals to give perfumers and other persons ability to create new fragrances for perfumes, colognes and personal care products.

Indancarbaldehyde and Indan-2-yl-carbaldehyde are known in the art. They are reported to be made by hydroformylation of indene. It is taught that the ratio of the two product isomers can be controlled by varying reaction temperature and catalyst (DE 2053736 and DE 2132414). It is also disclosed that indancarbaldehyde can be converted using standard chemical techniques to the corresponding alcohol and acetate (Doyle, Michael M. ; Jackson, Roy W; Perlmutter, Patrick, Tetrahedron Lett, 1989, 5357–5360), as well as the corresponding dimethylacetal (Corner, Avelino; Clement, Maria J.; Carcia, Hermenegildo; Primp, Jaime, Appl. Catal. 1990, 59(2), 33–40).

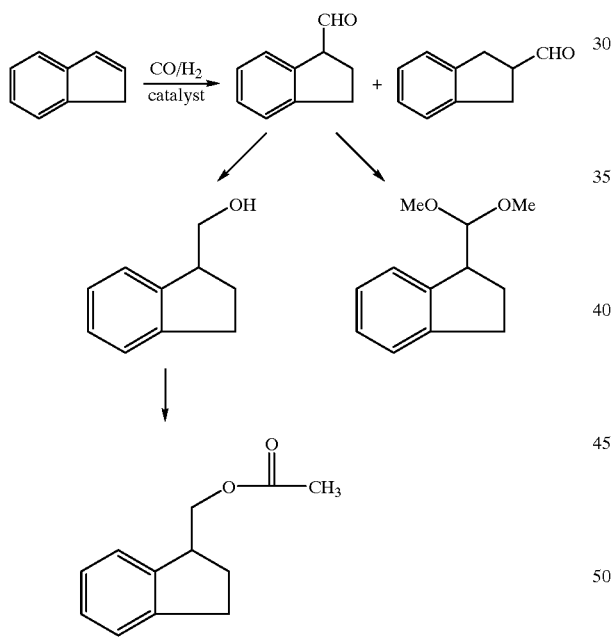

These materials as well as other derivatives of indancarbaldehyde and indan-2-yl-carbaldehyde have not been used in the fragrance industry or reported to show utility as aroma chemicals or fragrance enhancers. There is an ongoing need for the creation of new aroma chemicals that impart floral, fruity and woody "notes" or aromas to enhance fragrance formulations.

SUMMARY OF THE INVENTION

The present invention provides novel chemicals, and incorporation of these chemicals to provide a fragrance for perfumes, toilet waters, colognes personal products and the like. In addition, the present invention is directed to the use of related chemicals to enhance fragrance in perfumes, toilet waters, colognes, personal products and the like.

More specifically, the present invention is directed to new compounds of the formulae:

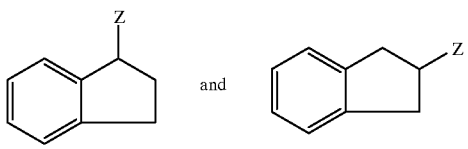

which can be represented by

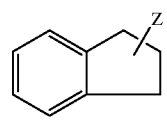

where Z is selected from the group consisting of:

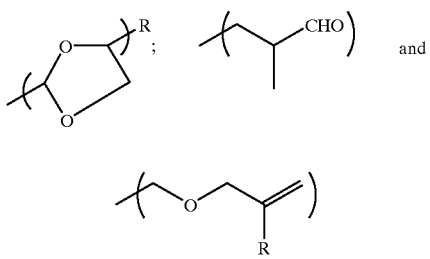

where R=H or methyl

Another embodiment of the invention is a method for enhancing a perfume by incorporating an olfactory acceptable amount of compounds of the formula:

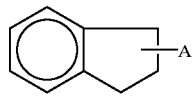

where A is selected from the group selected consisting of:

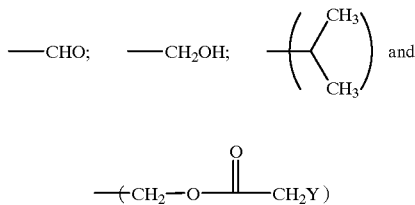

where
R is H or methyl
and Y is selected from the group consisting of H, $CH_3$, $C_2H_5$, and $C_3H_7$.

These and other embodiments of the present invention will be apparent by reading the following specification.

DETAILED DESCRIPTION OF THE INVENTION

The present invention is directed to the following novel chemicals of the structures, the processes for synthesizing these novel materials, and their use in perfume formulation:

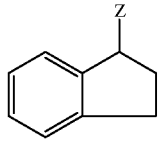 and 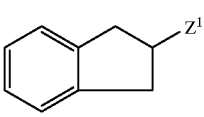

where the Z or $Z^1$ element is shown below.

In addition to the compounds listed above, the present invention is directed to the use of the following compounds in fragrance formulations. These have the structures:

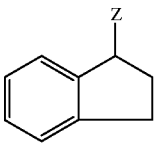 and 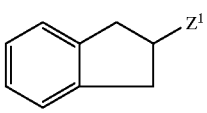

The Z and $Z^1$ element are as shown below:

| | IUPAC Name |
|---|---|
| Z element | |
| ![structure] | 2-indanyl-4-methyl-1,3-dioxolane |
| ![structure] | 2-indanyl-1,3-dioxolane |
| ![structure] | 3-indanyl-2-methylpropanal |
| ![structure] | 1-(indanylmethoxy)prop-2-ene |
| ![structure] | 1(indanylmethoxy)-2-methylprop-2-ene |
| $Z^1$ element | |
| ![structure] | 2-indan-2-yl-4-methyl-1,3-dioxolane |
| ![structure] | 2-indan-2-yl-1,3-dioxolane |
| ![structure] | 3-indan-2-yl-2-methylpropanal |
| ![structure] | 1-(indan-2-yl-methoxy)prop-2-ene |
| ![structure] | 1-(indan-2-yl-methoxy)-2-methylprop-2-ene |

| Z element | IUPAC name |
|---|---|
| —CHO | Indancarbaldehyde |
| ![structure with OCH₃, OCH₃] | Indandimethoxymethane |
| ![structure O-C(O)-CH₃] | Indanmethyl acetate |
| ![structure O-C(O)-CH₂CH₃] | Indanmethyl propionate |
| —(OH) | Indanmethanol |
| ![structure O-C(O)-CH₂CH₂CH₃] | Indanylmethylbutonate |
| —CHO | Indan-2-carbaldehyde |
| ![structure with OCH₃, OCH₃] | Indan-2-yl-dimethoxymethane |
| ![structure O-C(O)-CH₃] | Indan-2-yl-methylacetate |
| ![structure O-C(O)-CH₂CH₃] | Indan-2-yl-methylpropionate |
| —(OH) | Indan-2-yl-methanol |
| ![structure O-C(O)-CH₂CH₂CH₃] | Indan-2-yl-methylbutonate |

The positional isomers of each derivative may be used separately, or preferably as a mixture derived from indancarbaldehyde and indan-2-yl-carbaldehyde, formed in a ratio of 60/40 to 90/10. Those skilled in the art will appreciate that the corresponding isomer ratio of the specified derivative will be formed in a corresponding ratio.

The novel compounds of the present invention are prepared by the following reactions:

1. Dioxolane Derivatives

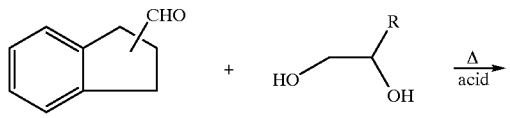

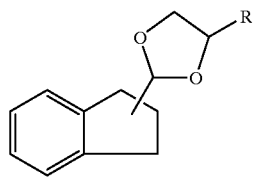

where $R = H$, methyl, or ethyl

In this reaction, the indancarbaldehyde isomers are reacted with a glycol, such as propylene glycol or ethylene glycol, in an inert solvent such as toluene, while being heated at reflux. An acid catalyst is employed to help catalyze the reaction. Water is removed via azeotropic distillation to drive the reaction to completion.

2. Condensation Reactions

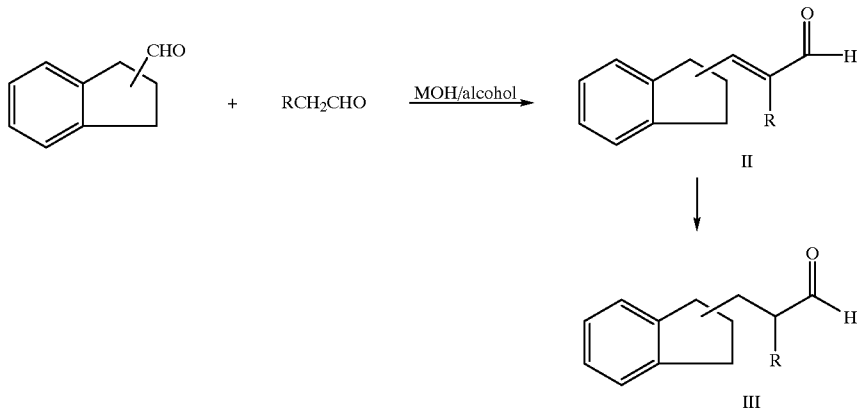

The mixture of indancarbaldehyde and indan-2-yl-carbaldehyde is reacted with aldehydes (wherein R=methyl, ethyl, propyl, isopropyl) in the presence of an alkali hydroxide (M=sodium, lithium, or potassium) in an alcoholic solvent (methanol, ethanol, isopropanol) to form the unsaturated carbonyl compound II. Carbonyl compound II may be reduced by catalytic hydrogenation over a suitable catalyst (from the group Pd, Pt, Rh, or Ni) to form the corresponding saturated carbonyl compound III. A specific embodiment of this invention is the condensation of propionaldehyde with indancarbaldehyde/indan-2-yl-carbaldehyde, followed by catalytic hydrogenation to form the corresponding indanylmethyl propanal derivatives V.

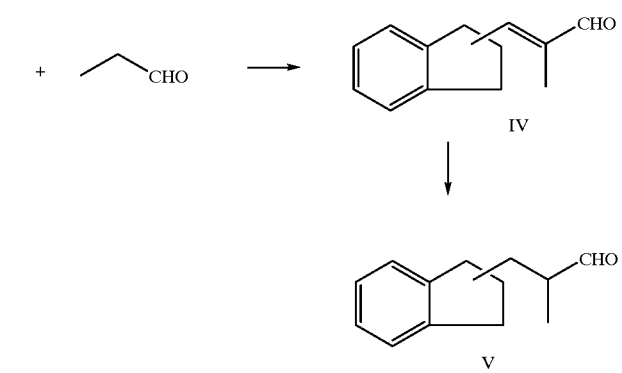

3. Ether Derivatives

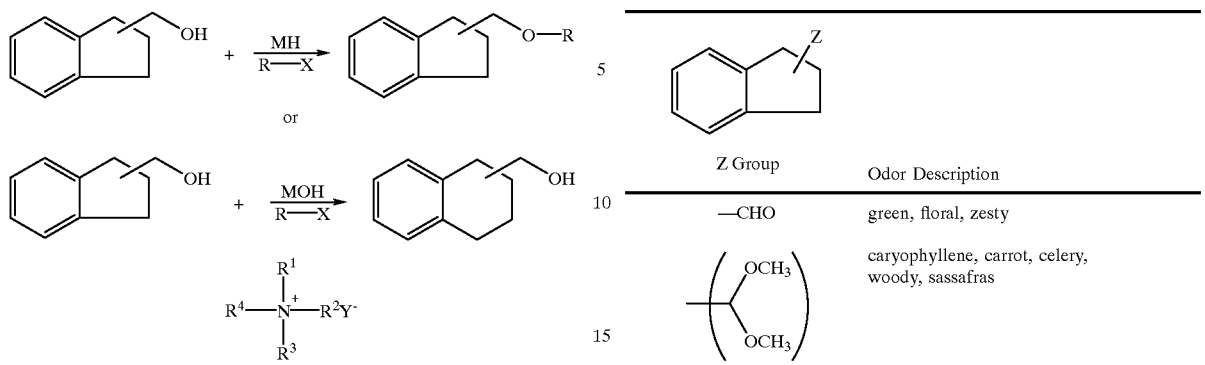

For these derivatives, a mixture of indanmethanol and indan-2-yl-methanol is reacted with an equivalent of a metal hydride (M=sodium, potassium, or lithium) and 1 to 2 equivalents of alkyl or alkenyl halide (R=methyl, ethyl, propyl, allyl, or 2-methylallyl, Y=chloride, bromide, iodide) in the presence of an inert solvent (such as tetrahydrofuran, dioxane, methylene chloride, toluene, and others) at a temperature ranging from 50° C. to 150° C.

Alternatively, the above ethers may be formed by reaction of the indan/indanyl carbaldehyde mixture with 1–2 equivalents of an alkyl or alkenyl halide, and 1–2 equivalents of an aqueous solution (25–50%) of a metal hydroxy base, in the presence of a phase transfer agent (1–10% by weight of the indanmethanol mixture) and an inert solvent (THF, toluene, methylene chloride, etc.). The temperature may vary between 45° C. and 90° C. Those skilled in the art will understand that a phase transfer agent refers to a tetralkyl ammonium salt where $R_1$ through $R_4$ may be the same or different saturated alkyl group, selected from $C_1$ and through $C_8$, and Y represents chloride, bromide, iodide, or sulfate.

In a specific embodiment of this invention, the indanmethanol mixture is reacted with allyl halide or a methallyl halide to form the corresponding ethers, VI and VII, respectively:

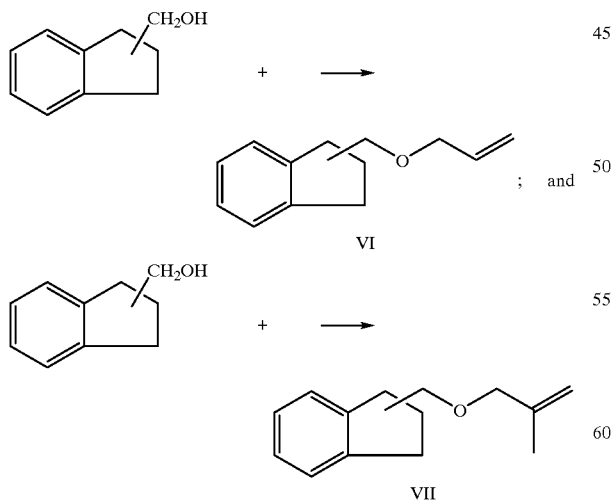

The odor characteristics of the specific chemicals presented in this invention are summarized in the following table.

| Z Group | Odor Description |
|---|---|
| —CHO | green, floral, zesty |
| —CH(OCH$_3$)$_2$ | caryophyllene, carrot, celery, woody, sassafras |
| —CH$_2$OH | green tea, rosy, musky, wood |
| —O—C(O)—CH$_3$ | floral, rosy with precious wood undertones |
| (tetrahydrofuran-2-yl) | green, woody, ozone |
| (methyl-dioxolane) | green, woody, terpenic |
| —O—CH$_2$—CH=CH$_2$ | green, spicy, floral cinnamic |
| —O—CH$_2$—C(CH$_3$)=CH$_2$ | green, hyacinth, galbanum, rhubarb |
| —CH(CH$_3$)—CHO | woody, fruity, green, leafy, fresh |
| —O—C(O)—CH$_2$CH$_3$ | floral, rose, woody |

The use of the these compounds is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients are known by those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps,* Second Edition, edited by W. A. Pouchier, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchide, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect which is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other amodifications of this invention will be readily apparent to those skilled in the art without departing from the scope of this invention. As used herein all percentages are weight percent and g is understood to be grams. IFF as used in the examples is understood to mean International Flavors & Fragrances Inc.

EXAMPLE 1

Reaction to produce a mixture of 3-indanyl-2-methylpropanol and 3-indan-2-yl-2-methylpropanol 290 Grams of propionaldehyde are added over 3 hours at 25° C. to a solution of 740 grams of a mixture of 90% indanecarbaldehyde and 10% indan-2-yl-carbaldehyde, in 24 grams of potassium hydroxide and 1480 grams of methanol. The reaction is stirred for 30 minutes and neutralized by adding 40 grams of acetic acid. The crude mixture is distilled to provide 420 grams of the indancarbaldehyde mixture and 242 grams of a mixture consisting of 90% 3-indanyl-2-methylprop-2-enal and 20% of 3-indan-2-yl-2-methylprop-2-enal (boiling point 138° C. at 1 millimeter of mercury).

The mixture is hydrogenated over 1.2 grams of 5 weight percent palladium on carbon catalyst at 110° C., 300 pounds per square inch hydrogen pressure for four hours. The crude product is filtered and distilled to provide 228 grams of 90% 3-indanyl-2-methyl propanol and 20% 3-indan-2-yl-methyl propanal., boiling point 136° C. at1 mm Hg. NMR analysis: 1.15–1.19 ppm (dd, J=2,7 Hz, 3H), 1.38–1.96, 2.20–2.60 ppm (mm, 5H, 2.75–3.25 ppm (m,3H), 7.08–7.25 ppm (m, 4H), 9.62, 9.66 ppm (dd, J=2 Hz, 1H).

EXAMPLE 2

Preparation of a mixture indanmethyl propionate and indan-2-yl-methyl propionate Two hundred ten grams of a mixture of 70% indan-2-carbaldehyde and 30% indan-2-yl carbaldehyde and 208 grams of propionic anhydride are heated at reflux (130° C.) for two hours. The reaction mixture is cooled to 90° C. and treated with 500 milliliters of water. The aqueous layer is discarded and the organic layer was washed twice with 500 ml of 10% sodium carbonate solution. Distillation provides 168 grams of the above described product, having a boiling point of 103° C. at 1.2 mm of Hg.

NMR analysis of the product: 1.14 ppm (t, J=7.5 Hz, 3H), 1.78–1.90 ppm (m, 1H), 2.20–2.30 ppm (m,1 H), 2.35 ppm (q, J=7.5 Hz, 2H), 2.66–3.11 ppm (M,2H), 3.41–3.51 ppm (m,1H), 4.08–4.30 ppm (m,2H)7.1 1–7.30 ppm (m, 4H).

EXAMPLE 3

Preparation of a mixture of1-(indanylmethoxy)-2-methyprop-2-ene and 1-(indan-2-yl-methoxy)-2-methylprop-2-ene Two hundred eighty-six grams of 70% indanmethanol and 30% indan-2-yl-methanol is fed into a stirred slurry of 67 grams of sodium hydride (55% weight percent in mineral oil emulsion) in 800 milliliters of tetrahydrofuran (THF) over a one hour period at 50° C. The solution is stirred until hydrogen elimination ceases. Methallyl chloride (139 grams) is fed into the solution at 50° C. over two hours. The reaction mixture is stirred at 50° C. for one hour. Acetic acid (60 grams) is added and the TIF is distilled out of the solution to a pot temperature of 90° C. at one atmosphere. The organic reaction mixture was washed with 1000 milliliters of water and distilled to provide 334 grams of a 70/30 mixture of the above titled product (b.p. 109° C. at 3 mm).

The NMR analysis is as follows: 1.74 ppm (s, 3H), 1.79–1.02 ppm (m, 1H), 2.19–2.34 ppm (m,1H), 2.66–3.12 ppm (m, 2H), 3.43 (m, 2H), 3.55–3.65 ppm (m, 1H), 3.91 ppm (s, 2H), 4.88 ppm (s, 1H) 4.96 (s, 1H), 7.07–7.32 ppm (m, 4H).

EXAMPLE 4

Preparation of a mixture of 1-(indanylmethoxy) prop-2-ene and 1-(indan-2-yl-methoxy)prop-2-ene A mixture of 70% indanmethanol and 30% indan-2-yl-methanol is fed into a stirred slurry of 82 grams of sodium hydroxide (55 weight % emulsion in mineral oil) in 800 milliliters of THF over a one hour period at 50° C. The solution is stirred until hydrogen elimination ceases. Allyl chloride (118 grams) is fed into the resulting solution at 50° C. over two hours. The reaction mixture is stirred at 50° C. for an additional hour. Acetic acid (60 grams) is added and the THF is distilled out of the reaction mixture to a pot temperature of 90° C. at one atmosphere. The organic reaction mass is washed with 1000 milliliters of water and distilled to afford 285 grams of the above-titled ether (b.p. 105° C. at 3 mm).

NMR analysis: 1.79–1.92 ppm (m, 1H), 2.19–2.31 ppm (m, 1H), 2.68–3.12 ppm (m, 2H), 3.38–3.51 ppm (m, 2H), 3.59–3.68 ppm (m, 1H) 4.03 ppm (dd, J=1.3, 5.7 Hz, 2H), 5.20 ppm (d, J=9.8, 1H), 5.28 ppm (d, J=17 Hz, 1H), 5.86–5.99 (m, 1H), 7.08–7.32 ppm (m, 4H).

EXAMPLE 5

Preparation of a mixture of 2-indanyl 1,3-dioxolane and 2-indan-2yl-1,3-dioxolane A solution of 297 grams of a mixture of 70% Indancarbaldehyde and 30% indan-2-carbaldehyde, 300 grams of ethylene glycol, 6 grams of p-toluenesulfonic acid and 300 grams of toluene are heated 2 hours at reflux using a Dean-Stark trap to separate water. The mixture is cooled and washed with 200 milliliters of a 5 weight % sodium carbonate solution. The organic layer is distilled to provide 321 grams of 2-indanyl-4-methyl-1,3-dioxolane (b.p.121° C. at 3 mm).

NMR: analysis 1.21–1.31 ppm (m, 3H), 1.98–2.30 ppm (m, 2H, 2.79–3.10 ppm (m, 2H), 3.31–3.43 ppm (m, 2H), 3.88–4.26 ppm (m, 2H), 4.97–5.14 ppm (m, 1H), 7.07–747 (m, 4H).

EXAMPLE 6

Preparation of a mixture of 70% 2-indanyl-4-methyl-1,3-dioxolane and 30% 2-indan-2-yl-4-methyl-1.3-dioxolane.

A solution of 297 grams of 70% indane carbaldehyde and 30% indan-2-carbaldehyde, 300 grams of 1,2-propylene glycol, 6 grams of p-toluenesulfonic acid, and 300 grams of toluene are heated 2 hours at reflux using a Dean Stark trap to separate water. The mixture is cooled and washed with 200 milliliters of 5 weight % sodium carbonate solution. The organic layer is distilled to afford 286 grams of the titled mixture (b.p. 113° C. at 3 mm).

NMR analysis: 1.99–2.11 ppm (m, 1H), 2.16–2.25 ppm (m, 1H), 2.78–3.07 ppm (m, 2H), 3.39 ppm (dt, J=5, 8 Hz, 1H), 3.79–3.99 ppm (m, 4H), 4.95 ppm (d, J=5 Hz, 1H), 7.08–7.45 ppm (m, 4H).

EXAMPLE 7

Fragrance use of indancarbaldehyde and indan-2-yl-carbaldehyde

A mixture of 90% indancarbaldehyde and 10% indan-2-yl-carbaldehyde was incorporated into a rose-floral fragrance.

| Material | Parts |
| --- | --- |
| Hedione ® (Firmenich) | 60.0 |
| Iso-E Super ® (IFF) | 10.0 |
| Linalool | 15.0 |

-continued

| Material | Parts |
| --- | --- |
| Phenyl Ethyl Alcohol | 10.0 |
| Diethyl Phthalate | 4.5 |
| Mixture of 90% indancarbaldehyde and 10% indan-2-yl-carbaldehyde | 0.5 |

EXAMPLE 8

Incorporation of a mixture of 3 indanyl-2-methylpropanol and 3-indan-2-yl-2-methylpropanal into a fragrance

| Material | Parts |
| --- | --- |
| Lilial ® (Givaudan) | 100 |
| Citronenellol | 75 |
| Amyl cinnamic aldehyde | 75 |
| Galaxolide 50 ® (IFF) | 200 |
| p-t-butylcyclohexylacetate | 80 |
| Rose oxide | 10 |
| Cinnamic alcohol | 20 |
| Bacdanol ® (IFF) | 100 |
| Phenyl ethyl alcohol | 50 |
| Limonene | 10 |
| Vertivert acetate | 10 |
| Dimethyl phthalate | 100 |
| Dihydromyrcenol | 100 |
| Ylang oil | 20 |
| The mixture of 3-indanyl-2-methyl propanol and 3-indan-2-yl-2-methyl propanal as prepared in Example 1 | 50 |

EXAMPLE 9

Incorporation of a mixture of 70% indanmethanol and 30% indan-2-ylmethanol into a fragrance

| Material | Parts |
| --- | --- |
| Hedione ® (Firmenich) | 300 |
| Galaxolide 50 ® (IFF) | 200 |
| Linallyl acetate | 50 |
| Geranyl acetate | 100 |
| Hydroxycitronellol | 100 |
| Bacdanol ® (IFF) | 50 |
| Iso-E Super ® | 50 |
| A mixture of 70% indanmethanol and 30% indan-2-yl-methanol | 150 |

EXAMPLE 10

Incorporation of a mixture of 70% indanmethyl acetate and 30% indan-2-yl-methyl acetate into a fragrance

| Material | Parts |
| --- | --- |
| Hedione ® (Firmenich) | 300 |
| Galaxolide 50 ® (IFF) | 200 |
| Linallyl acetate | 50 |
| Geranyl acetate | 100 |

-continued

| Material | Parts |
| --- | --- |
| Hydroxycitronellol | 100 |
| Bacdanol ® (IFF) | 50 |
| Iso-E Super ® | 50 |
| A mixture of 70% indanmethyl acetate and 30% indan-2-ylmethyl acetate | 150 |

EXAMPLE 11

Incorporation of a mixture of 70% indanmethyl propionate and 30% indan-2-yl-propionate into a fragrance formula

| Material | Parts |
| --- | --- |
| Hedione ® (Firmenich) | 300 |
| Galaxolide 50 ® (IFF) | 200 |
| Linallyl acetate | 50 |
| Geranyl acetate | 100 |
| Hydroxycitronellol | 100 |
| Bacdanol ® (IFF) | 50 |
| Iso-E Super ® | 50 |
| A mixture of 70% indanmethyl propionate and 30% indan-2-yl-propionate as prepared in Example 2 | 150 |

EXAMPLE 12

Incorporation of a mixture of 70% 1-(indanylmethoxy)prop-2-ene and 1-(indan-2-yl-methoxy) prop-2-ene into a fragrance

| Material | Parts |
| --- | --- |
| Ylang oil | 5 |
| Geraniol | 100 |
| Citronellol | 50 |
| Dimethyl benzyl carbinol | 70 |
| Phenyl ethyl alcohol | 30 |
| Hexylcinnamic aldehyde | 50 |
| Linallyl acetate | 50 |
| Galaxolide 50 ® (IFF) | 200 |
| Bacdanol ® | 50 |
| Lavender oil | 10 |
| Geranyl nitrite | 50 |
| Lyral ® (IFF) | 20 |
| Hedione ® (Firmenich) | 50 |
| Lilial ® (Givaudan) | 100 |
| A mixture of 70% 1-(indanylmethoxy) prop-2-ene and 1-(indan-2-yl-methoxy) prop-2-ene | 4 |

EXAMPLE 13

Incorporation of a mixture of 70% 1-indanylmethoxy)-2-methprop-2-ene and 1-(indan-2-yl-methoxy)-2-methprop-2-ene into a fragrance formulation

| Material | Parts |
| --- | --- |
| Ylang oil | 10 |
| Geraniol | 100 |
| Citronellol | 50 |
| Dimethyl benzyl carbinol | 70 |
| Phenyl ether alcohol | 30 |
| Hexylcinnamic aldehyde | 50 |
| Linallyl acetate | 50 |
| Galaxolide 50 ® (IFF) | 200 |
| Iso-E Super ® (IFF) | 100 |
| Bacdanol ® | 50 |
| Lavender oil | 10 |
| Oranyl oil | 15 |
| Lyral ® (IFF) | 50 |
| Hedione ® (Firmenich) | 50 |
| Lilial ® (Givaudan) | 100 |
| A mixture of 70% 1-(indanylmethoxy)-2-methprop-2-ene and 1-(indan-2-yl-methoxy)-2-methprop-2-ene | 45 |

EXAMPLE 14

Incorporation of a mixture of 70%-2-indanyl-1,3-dioxolane and 30% 2-indan-2-yl-1,3-dioxolane into a fragrance formulation

| Material | Parts |
| --- | --- |
| Hedione ® (Firmenich) | 150 |
| Galaxolide 50 ® (IFF) | 150 |
| Iso-E Super ® (IFF) | 150 |
| Vanillin | 20 |
| Phenyl ethyl alcohol | 50 |
| Linalool | 90 |
| Geraniol | 150 |
| Geranyl acetate | 150 |
| A mixture of 70% indanyl-1,3-dioxolane and 30% 2-indan-2-yl-1,3-dioxolane (as prepared in Example 5) | 80 |

EXAMPLE 15

Incorporation of a mixture of 70% 1-(indanylmethoxy)prop-2-ene and 2-(indan-2-yl-methoxy)prop-2-ene into a fragrance formulation

| Material | Parts |
| --- | --- |
| Methyl dihydrojasmonate | 150 |
| Galaxolide 50 ® (IFF) | 150 |
| Iso-E Super ® (IFF) | 150 |
| Vanillin | 10 |
| Phenyl ethyl alcohol | 50 |
| Linalool | 90 |
| Geraniol | 150 |
| Geranyl acetate | 150 |

-continued

| Material | Parts |
|---|---|
| A mixture of 70% 1-(indanylmethoxy) prop-2-ene and 30% 1-(indan-2-yl-methoxy) prop-2-ene (as prepared in Example 4) | 100 |

The above fragrance formulations are presented to demonstrate the effectiveness of the compounds of the present invention in enhancing, improving or modifying the performance of the formulations in which they are incorporated.

What is claimed is:

1. A method for improving, enhancing or modifying the odor properties of a fragrance by incorporating an olfactory acceptable amount of a compound of the formula:

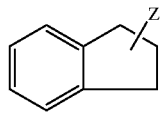

where Z is selected from the group consisting of:

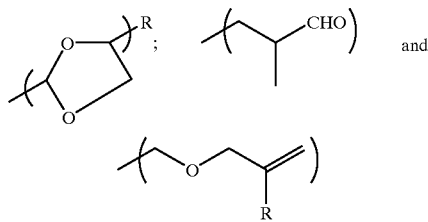

and where R=H or $CH_3$; and

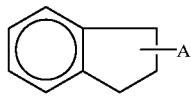

where A is selected from the group selected consisting of:

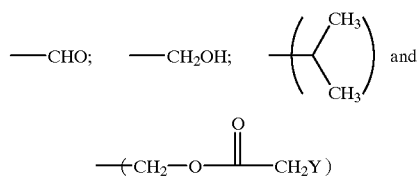

where
R is H or $CH_3$;
and Y is selected from the group consisting of H, $CH_3$; $C_2H_5$; and $C_3H_7$.

2. The method of claim 1 wherein the compound is selected from the group consisting of 2-indanyl-1,3-dioxane,
2-indanyl-4-methyl-1,3-dioxolane,
2-indan-2-yl-1,3-dioxalane,
3-indanyl-2-yl-2-methylpropanal,
indancarbaldehyde,
indanmethanol,
indan-2-carbaldehyde,
indan-2-yl-methanol, and
indan-2-yl-methyl butonate.

3. The method of claim 2 wherein the compound is selected form the group consisting of 3-indanyl-2-methylpropanal,
3-indan-2-yl-2-methylpropanal,
indancarbaldehyde,
indanmethanol,
indan-2-carbaldehyde and
indan-2-yl-methanol.

4. The method of claim 1 wherein the fragrance is incorporated into a product selected from perfumes, colognes, toilet waters, personal care products, cleaning products and air fresheners.

5. The method of claim 4 wherein the cleaning product is selected from the group consisting of detergents, dishwashing compositions, scrubbing compounds and window cleaners.

6. The method of claim 1 wherein the product is a personal care product.

* * * * *